United States Patent [19]

Manwaring et al.

[11] Patent Number: 5,638,819
[45] Date of Patent: Jun. 17, 1997

[54] METHOD AND APPARATUS FOR GUIDING AN INSTRUMENT TO A TARGET

[76] Inventors: Kim H. Manwaring, 3440 E. Tonto Dr., Ahwatukee, Ariz. 85044; Mark L. Manwaring, SW. 1430 Wadleigh Dr., Pullman, Wash. 99163

[21] Appl. No.: 520,386

[22] Filed: Aug. 29, 1995

[51] Int. Cl.$^6$ .............. A61B 5/05; G02B 23/26
[52] U.S. Cl. .......... 128/653.1; 600/103; 600/117
[58] Field of Search ............. 128/653.1; 600/103, 600/109, 117, 160, 166; 364/413.13, 413.14; 606/130

[56] References Cited

U.S. PATENT DOCUMENTS

| | | | |
|---|---|---|---|
| 4,608,977 | 9/1986 | Brown | 128/303 B |
| 4,791,934 | 12/1988 | Brunnett | 128/653 |
| 4,902,129 | 2/1990 | Siegmund et al. | 600/103 |
| 5,099,846 | 3/1992 | Hardy | 128/653.1 |
| 5,142,930 | 9/1992 | Allen et al. | 74/469 |
| 5,305,203 | 4/1994 | Raab | 606/130 |
| 5,330,485 | 7/1994 | Clayman et al. | 606/130 |
| 5,383,454 | 1/1995 | Bucholz | 128/653.1 |
| 5,515,160 | 5/1996 | Schulz et al. | 600/117 |

FOREIGN PATENT DOCUMENTS

| | | | |
|---|---|---|---|
| 00457 | 5/1988 | Germany | A61B 19/00 |

OTHER PUBLICATIONS

Three–Dimensional Digitizer (Neuronavigator) : New Equipment For Computed Tomography–Guided Stereotaxic Surgery. Wanatabem et al. 27 Surg. Neurol 543–7 (1987).

A Frameless, armless navigational systme for computer–assisted neurosurgery. Kato, et al., Neurosurg/ vol. 74/ May 1991.

Fowler Rebecca, "Computers May Drive Revolution in Neurosurgery Techniques", *The Washington Post*, Science & Medicine Section, p. A3, Monday, Aug. 15, 1994.

*Primary Examiner*—William E. Kamm
*Assistant Examiner*—Carl H. Layno
*Attorney, Agent, or Firm*—Meschkow & Gresham, P.L.C.

[57] ABSTRACT

A system (10) presents a graphic guidance object (46) in a display screen (40) to aid a surgeon in guiding a probe (12) from an initial point (82) relative to a body (14) along a desired trajectory (54) to a target (52). The graphic object (46) may be presented simultaneously with a live video image (44) from an endoscope and with tomogram images (42). The graphic object (46) includes a probe tip indicator (88) and a trajectory indicator (94). These indicators (88, 94) are positioned relative to one another to graphically indicate how far and in which direction to move a probe tip (36) to cause the probe tip (36) to intersect the desired trajectory (54). A roll orientation feature (118) and a distance-to-target feature (126) are included in the graphic object (46). The graphic object (46) changes in real time to track movement of the probe (12).

15 Claims, 5 Drawing Sheets

METHOD AND APPARATUS FOR GUIDING AN INSTRUMENT TO A TARGET

TECHNICAL FIELD OF THE INVENTION

The present invention relates generally to the field of surgery. More specifically, the present invention relates to devices and techniques for guiding a surgical instrument to a target within a body part.

BACKGROUND OF THE INVENTION

Less invasive surgery techniques are usually more desirable than more invasive techniques because the patient suffers less trauma, suffers fewer side effects, and heals quicker. For a given pathology, endoscopic surgery is often less invasive than other surgical options. In endoscopic surgery, a surgeon guides a relatively small endoscope configured as a probe to a target region of a body part. The endoscope generates live video images of anatomy encountered at the tip of the probe, and the surgeon uses these video images as an aid in guiding the probe to the target region. Similarly, a guided microscope can be employed to show where a variety of instruments should be applied. Once the probe has been guided to the target, a variety of surgical techniques may then be performed at the target region.

However, endoscopic surgery has conventionally been considered too dangerous where few distinctive visual features are available within a subject body part. When few distinctive visual features are available, the surgeon risks becoming disoriented while guiding the probe to the target region. This disorientation may cause the surgeon to inflict extensive trauma on the patient while failing to reach the target region. Since few distinctive visual features are found in the interior of many internal organs, such as the brain, many pathologies have not been successfully operated upon endoscopically.

Endoscopic surgery within the brain has often been considered exceptionally risky because a path followed by a probe in traversing from outside the body to a target region, for example a tumor, should avoid critical or eloquent areas of the brain to the maximum extent possible to prevent permanent brain damage. Consequently, not only does a probe or needle need to be guided to a target region, but the probe should be guided to the target region over a specific route or trajectory. Disorientation and a resulting deviation from a specific trajectory may lead to severe consequences even when the target region is successfully reached.

Various systems and techniques have been devised to let a surgeon know the location of a surgical instrument within a body even though few visual clues may be available. For example, various framed and frameless stereotactic surgical techniques incorporate systems for informing a surgeon of an instrument position. When such position information is accurate, it may help a surgeon find a target region. However, mere position information fails to inform a surgeon about whether an instrument is on a specific trajectory, and such information fails to inform a surgeon of actions needed to cause an instrument to more closely approach a specific trajectory. Consequently, a high risk of disorientation still remains when limited visual clues are present.

In addition, various systems present tomogram images in combination with surgical instrument position information. For example, during surgery a surgical instrument's position may be superimposed or otherwise indicated on a tomogram which is viewable by the surgeon. These tomogram-based systems attempt to better inform a surgeon of whether an instrument is positioned as desired because a surgeon can view instrument position relative to an overall tomogram image.

However, tomograms represent anatomy at a past point in time and in a situation where the anatomy is not being influenced by the surgery itself. Tomograms fail to reveal actual anatomy at the instant of surgery and under the influence of surgery. Consequently, tomograms often fail to provide accurate anatomical renditions existing during surgery, and relative position information indicated on tomograms may not be accurate. Moreover, even if a tomogram-based system happens to accurately portray relative instrument position, nothing informs a surgeon about whether an instrument's position is consistent with a specific trajectory or about actions needed to cause an instrument to more closely achieve a specific trajectory.

Still other systems attempt to perform extensive 3-D computer enhancement and reconstruction of tomogram images during surgery in response to instrument position information in an attempt to better allow a surgeon to visualize instrument orientation and anatomy traversed by the surgical instrument. However, no amount of computer reconstruction can make tomogram images taken at a past point in time under non-surgical conditions to accurately portray anatomy under the influence of surgery. Moreover, complex 3-D computer analysis of tomogram images requires extensive computing power, causing a time lag between the actual instrument positioning and the resulting enhanced or reconstructed images. Such systems merely react to actions already taken by a surgeon and fail to adequately inform a surgeon of what future actions are needed to guide an instrument along a specific trajectory to a target region.

SUMMARY OF THE INVENTION

Accordingly, it is an advantage of the present invention that an improved method and apparatus for guiding an instrument to a target are provided.

Another advantage is that the present invention displays information to a user which indicates whether or not a surgical instrument is positioned along a specific trajectory.

Another advantage is that the present invention displays information to a user which indicates in which direction to move a probe tip to cause a probe tip to intersect a specific trajectory.

Another advantage is that the present invention automatically displays trajectory guidance information in real time.

Another advantage is that the present invention may combine trajectory guidance information with one or more of tomogram and endoscopic images.

The above and other advantages of the present invention are carried out in one form by a method for presenting guidance information to a user engaged in guiding a probe to a target within a body. The method calls for identifying a location for the target. A location for an initial point relative to the body is identified. A current location for a tip of a probe is determined. A graphic object is then displayed. The graphic object indicates a direction in which to move the probe tip to cause the probe tip to intersect a predetermined trajectory which includes the target and the initial point locations.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
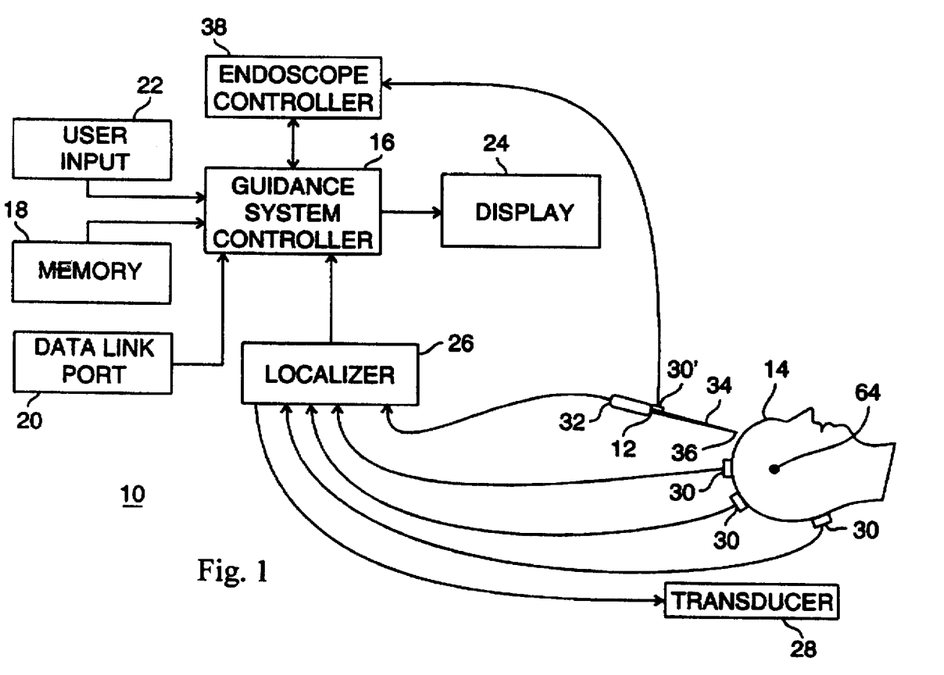
FIG. 1 shows a block diagram of a guidance system.

FIG. 1 shows a block diagram of a guidance system 10. Guidance system 10 provides information which aids the guidance of a probe 12 to a target located inside a body 14. Probe 12 represents any instrument which may be inserted into body 14. While any type of instrument constitutes probe 12 for purposes of the present invention, an endoscope represents one particularly desirable form of probe 12. FIG. 1 illustrates body 14 in the form of a human head because system 10 is particularly suited to endoscopic surgery within the brain. However, system 10 is not limited to brain or endoscopic surgeries. System 10 may be used to advantage in any surgery where a tool is desired which aids guiding probe 12 along a selected trajectory to a target.

System 10 includes a guidance system controller 16. Conventional medical, personal, or industrial computer components, such as a processor board, may serve as controller 16. Controller 16 couples to a memory 18, a data link port 20, a user input device 22, and a display unit 24. Memory 18, data link port 20, user input device 22, and display 24 all represent conventional computer components commonly used in connection with medical, personal, industrial, and other computers.

Memory 18 stores databases used by system 10 and computer programs which define the operation of system 10 along with other data items. Such databases may include digitized tomograms. The tomograms may be formed in accordance with conventional CT, MRI, PET, or other tomographic techniques. Portions of the computer programs which are relevant to the present invention are discussed below in connection with FIGS. 2–10.

Data link port 20 allows controller 16 to import external data. For example, port 20 may represent a LAN port, modem, removable disk drive, or tape drive. Among other data items, tomogram databases, which may be supplied by external radiology or other computers, are received through port 20.

User input device 22 allows a surgeon or other user of system 10 to enter selections and otherwise provide data to system 10. Such selections control the operation of system 10 before, during, and after surgery. Conventional touch screens, remote control devices, keyboards, pointing devices, and the like all represent suitable examples of user input device 22. However, user input device 22 is desirably located for easy manipulation by a surgeon during surgery and sterilized at least to the extent that it is manipulated by the surgeon.

Display 24 is desirably a CRT, LCD, plasma, or other video terminal or projection device which visually presents information to a surgeon or other user of system 10. Regardless of where other components of system 10 may be located, display 24 is desirably located so that its visually presented information may be conveniently viewed by a surgeon during surgery.

Controller 16 additionally couples to a localizer 26 through which controller 16 obtains location data. While the preferred embodiment of system 10 uses a magnetic location determination system, the present invention may be practiced using acoustic, infrared, mechanical, or other location determination systems known to those skilled in the art. Non-mechanical embodiments of such systems typically include a transducer 28 which provides an acoustic, optic, or magnetic reference. Using transducer 28, the location of various sensors 30 may be determined. Transducer 28 and sensors 30 couple to localizer 26 via flexible cabling.

A sensor 30' is located on a handle 32 of probe 12 and generates location data regarding the position of sensor 30'. Sensor 30' provides continuous roll, pitch, and yaw signals that track any movement in sensor 30'. Probe 12 includes a shaft 34 at the end of which resides a probe tip 36. For a given probe 12, tip 36 has a fixed spatial relationship to sensor 30'. Controller 16 tracks the location of a tip 36 based upon location data provided by sensor 30' and this fixed spatial relationship.

Controller 16 also couples to an endoscope controller 38. Controller 38 is a conventional device for controlling endoscope parameters. While not required, probe 12 is desirably fitted with an endoscope which couples to controller 38 so that forward-looking, live video images taken from tip 36 of probe 12 are available to system 10. Guidance system controller 16 couples to endoscope controller 38 to control endoscope parameters and to receive the resulting live video images.

System 10 may include other components which are not relevant to the present invention. Such other components may include a video recorder configured to record images appearing on display 24 during a surgery. Moreover, additional displays may be driven by controller 16.

Figure 2:
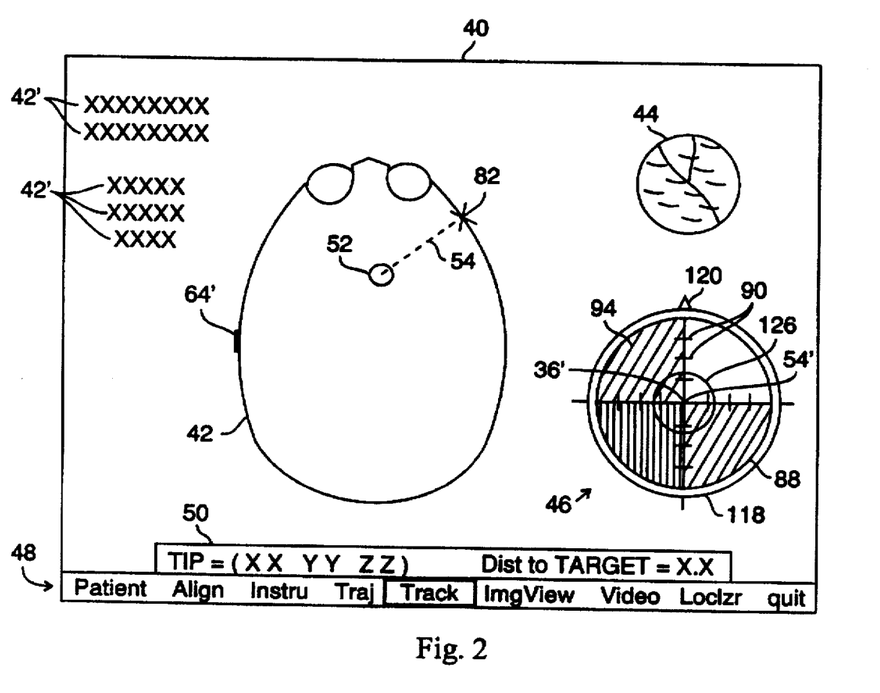
FIG. 2 shows a schematic view of a display presented to a user who is engaged in guiding a probe to a target within a body.

FIG. 2 shows a schematic view of an example display screen 40 presented to a surgeon engaged in guiding probe 12 to a target within body 14 (see FIG. 1). Screen 40 includes a tomogram slice 42, including associated alphanumeric data 42', a live video image 44, a graphic guidance object 46, a plurality of selection buttons 48, and alphanumeric position data 50.

Screen 40 is a tool to be used by a surgeon during surgery in any manner deemed appropriate by the surgeon. In a typical scenario, the surgeon's primary focus rests on graphic guidance object 46. Graphic object 46 changes in real time to track movement of probe 12 within body 14. Graphic object 46 includes several features which aid the surgeon in guiding tip 36 (see FIG. 1) of probe 12 to a target 52 along a desired trajectory 54. Generally, the relative orientation and positioning of these features indicate whether probe tip 36 currently resides on trajectory 54. If probe tip 36 does not reside on trajectory 54, then the relative orientation and positioning of these features indicate a direction in which to move probe tip 36 to cause probe tip 36 to intersect trajectory 54. These features are discussed in detail below.

In the typical scenario, the surgeon's secondary focus rests on live video image 44. When image 44 is generated by an endoscope, it informs a surgeon of structures actually and immediately in front of probe tip 36. In an alternate embodiment of the present invention, image 44 may be generated by a microscope (not shown). When a surgeon notices an artery or other critical structure, probe 12 may be maneuvered to avoid the structure. For surgeries within the interior of the brain and other organs, few visually distinctive structures may be seen in live video image 44 until probe 12 nears target 52. Consequently, image 44 typically receives a reduced level of attention by the surgeon relative to object 46.

In the typical scenario, the surgeon's tertiary focus rests on tomogram slice 42. Tomogram slice 42 provides a reference which may help the surgeon maintain a correct sense of orientation. Those skilled in the art will appreciate that various critical structures, such as arteries, may not be readily visible in the particular tomogram slice 42 showing on screen 40 at any given instant. Moreover, even if such structures are visible, they may not actually be located at the precise position during surgery where they were located during pre-surgery tomographic imaging. Consequently, tomogram slice 42 typically receives a reduced level of attention by the surgeon relative to object 46 and live video image 44.

FIG. 2 illustrates target 52 and trajectory 54 in connection with tomogram slice 42. However, those skilled in the art will appreciate that tomogram slice 42 is a 2-D image, that a typical target 52, such a tumor or the like, may very well be visible on only a few tomogram slice images out of an entire set of tomogram slice images, and that trajectory 54 may very well traverse a 3-D space relative to displayed tomogram slice 42. Accordingly, FIG. 2 illustrates only a projection of trajectory 54 on one particular tomogram slice 42 from a set of tomogram slice images.

Selection buttons 48 form a menu structure which may be logically traversed by the surgeon or other user of system 10 through manipulation of user input device 22 (see FIG. 1). User data provided through buttons 48 prior to surgery initialize system 10 for an upcoming surgery. During surgery these user-supplied data may alter program settings to accommodate events which may be encountered during the surgery. Alphanumeric position data 50 inform the user of the precise position of probe tip 36 in relation to an X,Y,Z coordinate system used by system 10 and of the distance between probe tip 36 and target 52 at any given instant.

Figure 3:
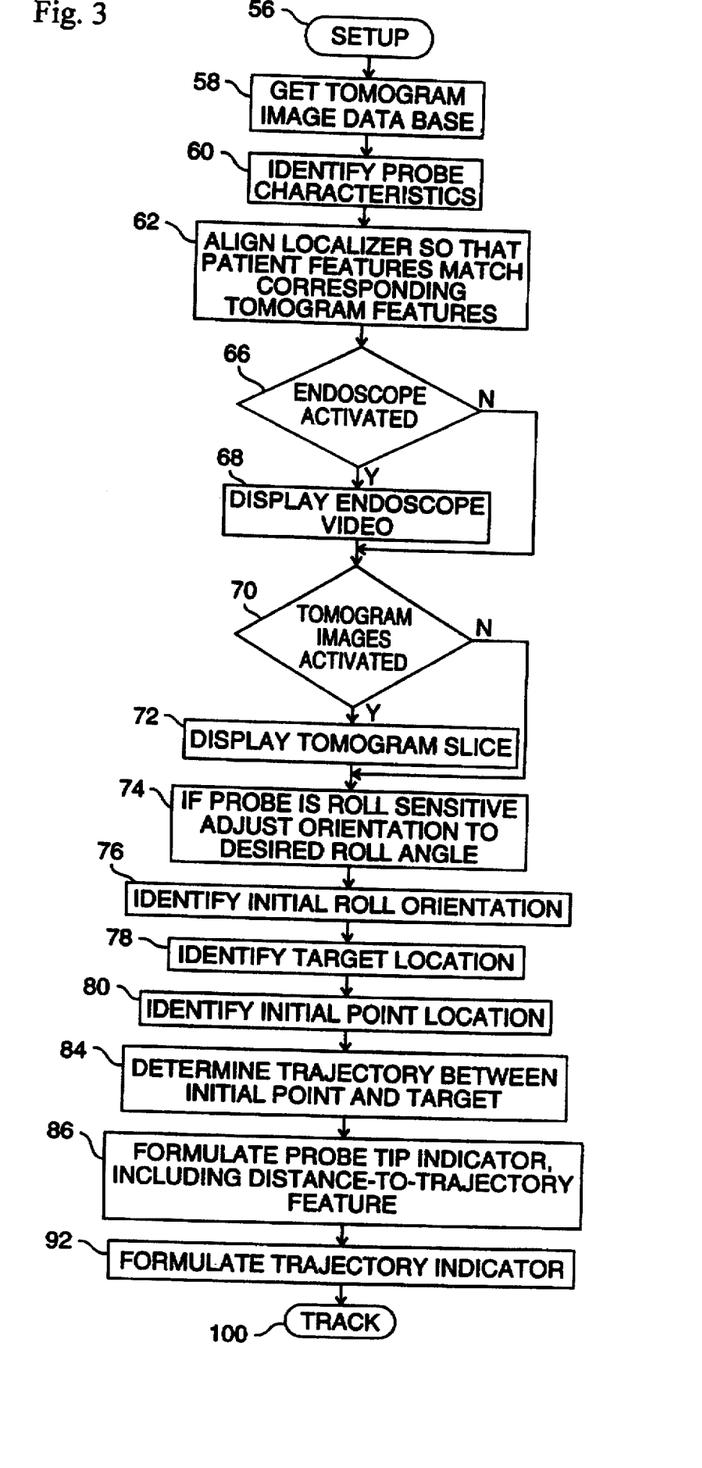
FIG. 3 shows a flow chart of a setup procedure performed by the guidance system.

FIG. 3 shows a flow chart of a setup procedure 56 performed by guidance system 10. Procedure 56 is performed interactively between a user of system 10 and controller 16 (see FIG. 1). Controller 16 performs its portion of procedure 56 under the control of a computer program stored in memory 18 (see FIG. 1). For convenience, FIG. 3 illustrates procedure 56 through a flow chart. However, many tasks performed during procedure 56 are independent of other tasks and need not be sequenced as indicated by this flow chart.

Procedure 56 includes a task 58 which gets a tomogram image database. Task 58 involves obtaining external tomogram data through data link port 20 (see FIG. 1) and having a user select the appropriate tomogram database. In the preferred embodiment, a tomogram database is selected by indicating a patient name which is associated with a particular tomogram database. In addition, nothing prevents multiple tomogram images from being obtained in task 58. Thus, a selected patient may have any number of CT, MRI, or PET image sets available for use during an upcoming surgery.

A task 60 identifies characteristics of a probe 12 to be used during an upcoming surgery. Task 60 may be performed when a user selects a particular make and model of surgical instrument from a menu selection of such instruments. Task 60 defines a specific spatial relationship between probe tip 36 and sensor 30' (see FIG. 1) which applies to the selected instrument. Thus, system 10 may compensate for variations in the length of the probe 12 and offsets between the axis of probe 12 and sensor 30' to accommodate a variety of different types of probes 12.

A task 62 aligns localizer data with tomogram imaging so that patient features match corresponding tomogram features. Referring back to FIGS. 1 and 2, task 62 may be performed by touching probe tip 36 to an alignment feature 64 fixed to the patient. Desirably, alignment feature 64 is configured to serve as a fiducial marker during tomographic imaging. Thus, one or more tomogram slices 42 depict an object 64' corresponding to feature 64. Alignment feature 64 desirably resides in a fixed position on the patient during pre-surgery imaging and during surgery. Feature 64 may be fixed by being attached to bone or by being attached to a mask worn by the patient during both imaging and surgery.

At any given instant, system 10 knows the location of probe tip 36 through the operation of localizer 26. By touching probe tip 36 to alignment feature 64 (see FIG. 1) while simultaneously identifying a pixel where object 64' (see FIG. 2) is depicted, system 10 may learn the position of alignment feature 64. Thereafter system 10 may translate between a coordinate system used by tomographic imaging and a coordinate system imposed by localizer 26 through the use of well known trigonometric relationships. Referring back to FIG. 3, at the conclusion of task 62 system 10 can obtain coordinates relative to localizer 26 for various points depicted on the aligned tomograms.

Procedure 56 includes a query task 66 that determines whether an endoscope is activated. As discussed above, probe 12 need not be an endoscope or contain an endoscope. However, if an endoscope is available, a task 68 causes live video image 44 (see FIG. 2) to be displayed. Live video image 44 will thereafter continue to be displayed. Likewise, procedure 56 includes a query task 70 that determines whether tomographic images 42 (see FIG. 2) have been activated for display on screen 40 (see FIG. 2). If activated, a task 72 causes a selected tomogram slice to be displayed.

Tasks 66 and 68 indicate that live video image 44 need not be displayed in all situations, and tasks 70 and 72 indicate that tomograph images 42 need not be displayed in all situations. Live video image 44 may be omitted, for example, when image 44 is unlikely to be useful due to endoscope clogging or when some other probe is being guided to target 52 (see FIG. 2). Tomograph images 42 may be omitted, for example, to allow larger viewing areas for the remaining items on display screen 40.

Procedure 56 includes a task 74 in which probe roll is adjusted to a desired angle when a roll sensitive probe 12 is used. Task 74 is primarily a manual step. Roll represents a clockwise or counterclockwise rotation around the axis of probe 12. An endoscope is one example of a roll-sensitive probe 12. Live video image 44 is oriented on display screen 40 in response to roll angle. Desirably, the top, bottom, right, and left sides of image 44 correspond to the top, bottom, right, and left sides, respectively, of probe tip 36 when probe 12 is held in its normal, operational orientation. Accordingly, during task 74 probe 12 is held normally and roll angle is adjusted to a desired orientation. Task 74 may be performed by observing a distinctive pattern, such as printed text, via both live video image 44 and the naked eye. The endoscope may be rotated so that the distinctive pattern shown in image 44 exhibits the same orientation observed by the naked eye.

A task 76 identifies this roll orientation as an initial roll orientation for system 10. In general, task 76 represents a counterpart of manual task 74 that is performed by system 10. At some time following completion of task 74, task 76 causes system 10 to record the roll orientation of probe 12.

Setup procedure 56 includes a task 78 in which a location for target 52 is identified. Target 52 may be identified when the user causes a tomogram slice 42 in which target 52 is visible to be displayed at display 24. When a tomographic image of target 52 is displayed, a user may cause a video display pointer, cursor, or the like to reside over the tomographic image of target 52. Using well known computer graphics techniques, the position of the tomographic target image relative to the tomogram coordinate system may be obtained from the location of pointer pixels. Due to alignment task 62 discussed above, this position may be translated into coordinates consistent with a coordinate system used by location system 26.

A task 80 identifies an initial point 82, illustrated in FIG. 2, for defining a desired trajectory 54 for probe 12 to follow in traversing body 14 to target 52. In accordance with conventional endoscopic surgery techniques, initial point 82 typically corresponds to an entry incision or burr hole into body 14 through which probe 12 will be guided to target 52. Task 80 may be performed when a user touches probe tip 36 to initial point 82 while simultaneously instructing system 10 to "grab" the coordinates of probe tip 36 for use as initial point 82. Initial point 82 is selected by the surgeon based upon the surgeon's experience, the particular pathology necessitating the surgery, and patient-specific anatomy considerations. In an alternate embodiment of the present invention, trajectory 54 may be coincident with an axis of a microscope. In this embodiment, initial point 82 may be outside the body somewhere along the axis of the microscope.

After the locations of target 52 and initial point 82 have been identified, a task 84 determines trajectory 54 so that trajectory 54 includes the coordinates of target 52 and initial point 82. In the preferred embodiment, trajectory 54 is a straight line segment extending between target 52 and initial point 82. A straight line trajectory accommodates typical probes 12, which have straight shafts 34 (see FIG. 1). However, straight line trajectories are not a requirement, and task 84 could alternatively define various configurations of curves to include coordinates for target 52 and initial point 82. Trajectory 54 desirably represents a curve defined through three-dimensional space in accordance with the coordinate system imposed by localizer 26.

Figure 4:
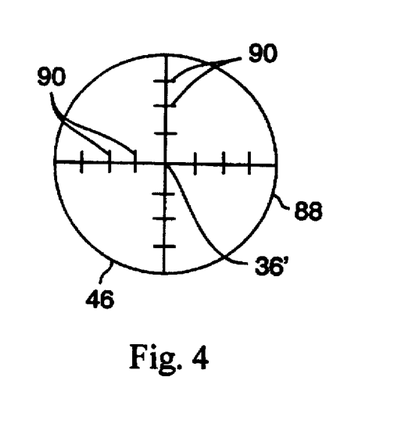
FIG. 4 shows a schematic view of a probe tip indicator feature of a graphic guidance object.

Setup procedure 56 includes a task 86 to formulate a probe tip indicator 88 of graphic object 46, schematically shown in FIGS. 2 and 4. Referring to FIGS. 2 and 4, probe tip indicator 88 desirably includes vertical and horizontal cross hairs residing within a circle. A probe tip point 36' resides at the intersection of the cross hairs. Probe tip point 36' represents the axis of probe 12 as it would be viewed looking down the axis of probe 12. The perimeter of probe tip indicator 88 is formed as a circle to resemble the perimeter shape of live video image 44 (see FIG. 2) from an endoscope.

In addition, probe tip indicator 88 includes a feature 90 for indicating distances to trajectory 54. In the preferred embodiment, feature 90 represents a set of hash marks on both the vertical and horizontal cross hairs of probe tip indicator 88. The hash marks are spaced apart to indicate a predetermined distance, preferably in the range of 0.25 to 1.0 cm. Nothing requires the hash marks to be spaced apart this predetermined distance in display screen 40. Once formulated, probe tip indicator 88 need not change. Accordingly, task 86 may be performed through software programming which need not be configured or altered in preparation for an upcoming surgery.

Figure 5:
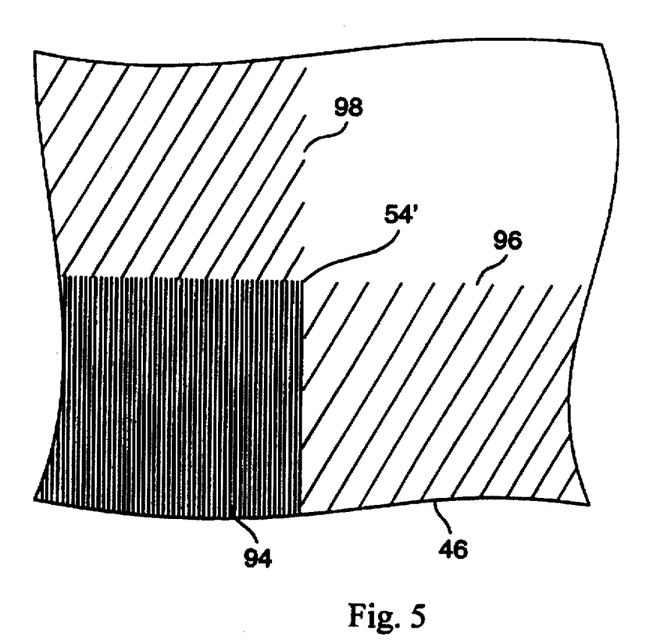
FIG. 5 shows a schematic view of a trajectory indicator included in the graphic object.

Likewise, a task 92 formulates a trajectory indicator 94, schematically shown in FIGS. 2 and 5. Trajectory indicator 94 is a logical construction and may be formulated through the structure of computer programming. Once formulated, the nature of trajectory indicator 94 need not change. Thus, task 92 may be performed through software programming which is not configured or altered in preparation for an upcoming surgery.

Referring to FIG. 5, in the preferred embodiment trajectory indicator 94 includes a horizontal pitch line 96 and a vertical yaw line 98, which together partition two-dimensional space into four quadrants. A trajectory point 54' resides at the intersection between pitch and yaw lines 96 and 98. Trajectory point 54' represents trajectory 54 as viewed looking from initial point 82 toward target 52 (see FIG. 2).

So that trajectory indicator 94 appears distinctively different from probe tip indicator 88 (see FIG. 4), pitch and yaw lines 96 and 98 need not actually be drawn. Rather, the four quadrants are defined to have contrasting colors. A light color is defined for an upper-right quadrant, medium colors are defined for lower-right and upper-left quadrants, and a dark color is defined for a lower-left quadrant. Consequently, pitch and yaw lines 96 and 98 and trajectory point 54' may be easily implied by the intersections between quadrants of contrasting colors. Moreover, lines 96 and 98 and trajectory point 54' may be easily distinguished from probe tip indicator 88 when overlaid thereon. FIG. 2 illustrates a situation where probe tip indicator 88 has been overlaid on trajectory indicator 94, and trajectory indicator 94 is aligned with probe tip indicator 88. Due to this alignment, the cross hairs of probe tip indicator 88 overlie pitch and yaw lines 96 and 98, and probe tip point 36' overlies trajectory point 54'. As shown in FIG. 2, any portion of trajectory indicator 94 which might have otherwise been viewable outside probe tip indicator 88 has been omitted from graphic object 46.

After completion of the above-discussed tasks included in procedure 56, system 10 may proceed to a track procedure 100, which is performed to assist the surgeon in the act of guiding probe tip 36 to target 52. However, system 10 proceeds to track procedure 100 only in response to user input, and such user input need not be provided until system 10 is completely setup. In other words, any of the above-discussed tasks included in procedure 56 may be repeated as desired until the surgeon is satisfied that system 10 and the surgeon are ready for surgery.

Figure 6:
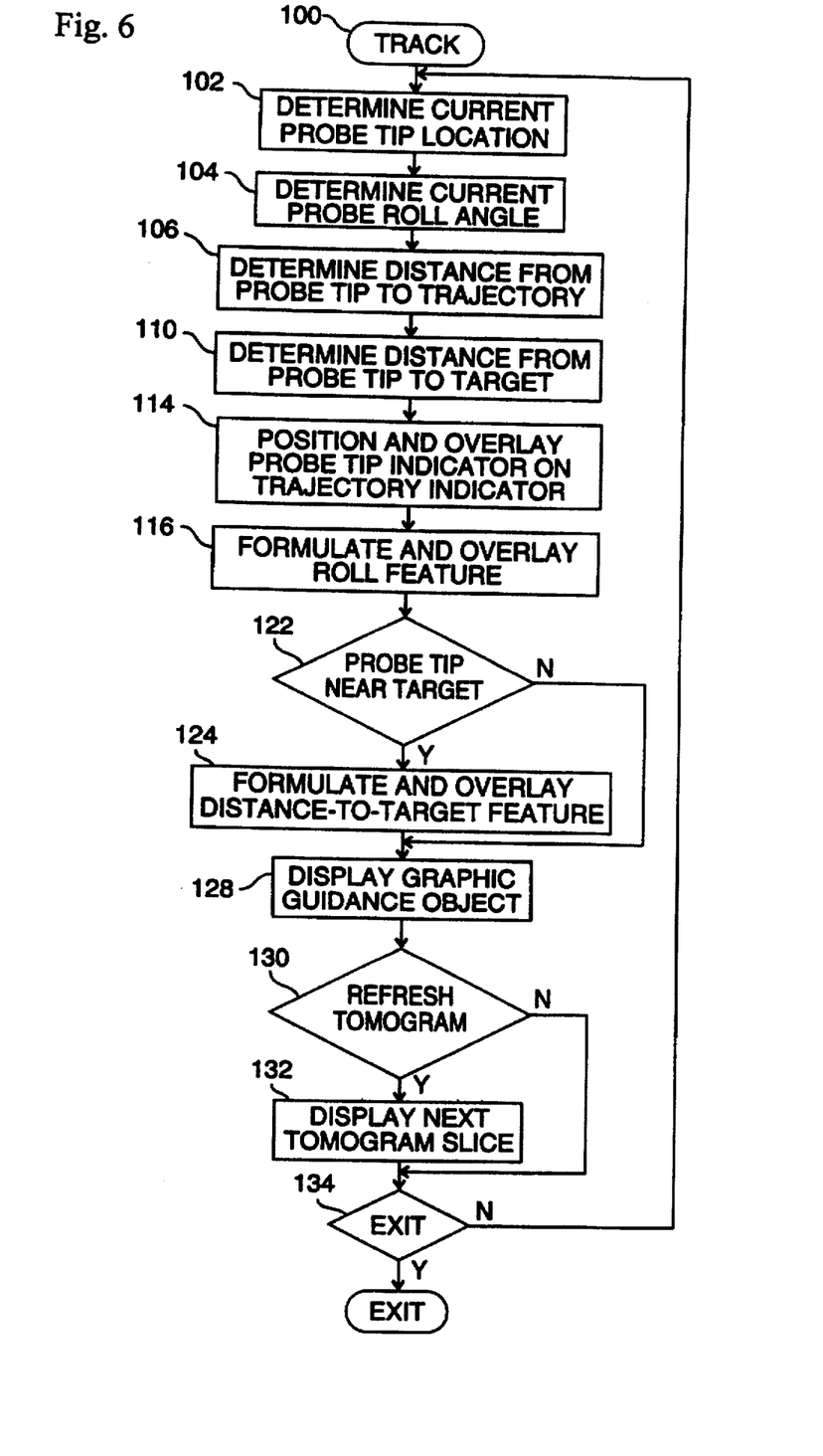
FIG. 6 shows a flow chart of a track procedure performed by the guidance system.

FIG. 6 shows a flow chart of track procedure 100. The operation of procedure 100 is described below in connection with FIG. 7, which shows geometric relationships between probe 12, initial point 82, and target 52 for a hypothetical situation. Those skilled in the art will appreciate that for clarity FIG. 7 shows only a two-dimensional projection of a three-dimensional geometry.

Figure 7:
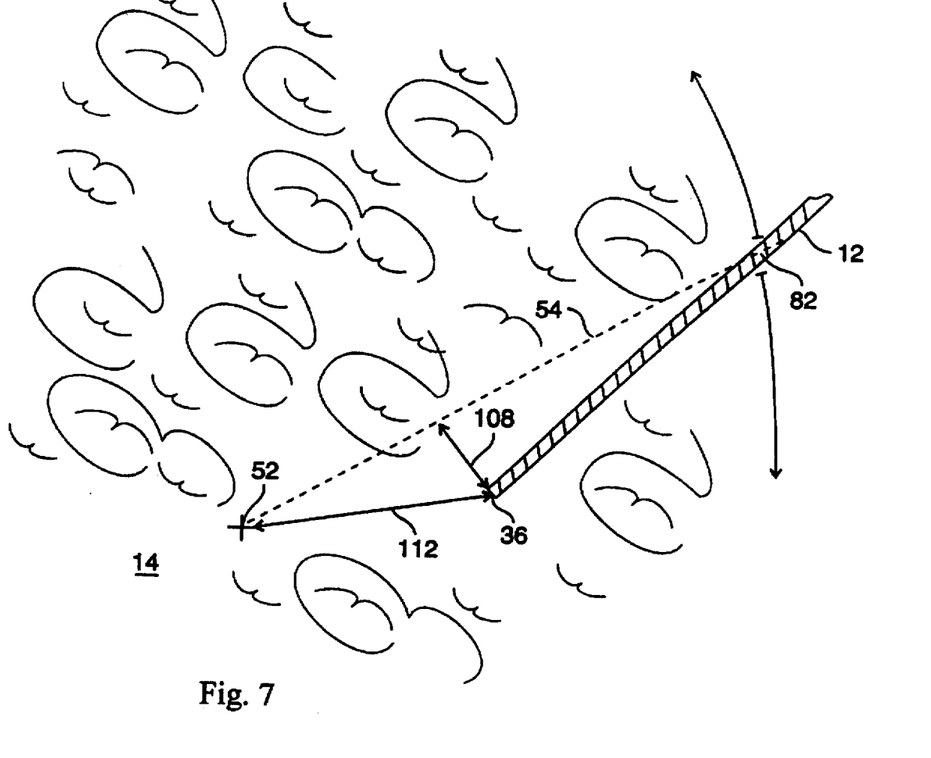
FIG. 7 shows exemplary geometrical relationships between a probe, an initial point, and a target.

Referring to FIGS. 6 and 7, procedure 100 includes a task 102 which determines the coordinates for a current location of probe tip 36. Task 102 is performed in response to location data provided from localizer 26 and sensor 30' (see FIG. 1). In the preferred embodiment, current coordinates for probe tip 36 are expressed in accordance with an X,Y,Z coordinate system established through the operation of localizer 26. After task 102, a task 104 determines a current probe roll angle. Roll angle is also determined in response to location data provided from localizer 26 and sensor 30'.

Next, a task 106 determines a distance 108 extending in a generally perpendicular direction from trajectory 54 to probe tip 36. Distance 108 may be determined in response to the trajectory defined above in task 84 (see FIG. 3) and to the current location for probe tip 36 determined above in task 102. Distance 108 represents the distance which probe tip 36 has deviated from the desired path to target 52. In addition, a task 110 determines a distance 112 between probe tip 36 and target 52. Distance 112 represents the additional distance yet to be traversed before probe tip 36 reaches target 52.

After tasks 106 and 110, a task 114 positions and overlays probe tip indicator 88 (see FIG. 4) on trajectory indicator 94 (see FIG. 5). Positioning is performed in response to the current position for probe tip 36 determined above in task 102 and in response to trajectory 54 defined above in task 84 (see FIG. 3). Any portion of trajectory indicator 94 which extends beyond the perimeter circle of probe tip indicator 88 may be omitted.

Figure 8:
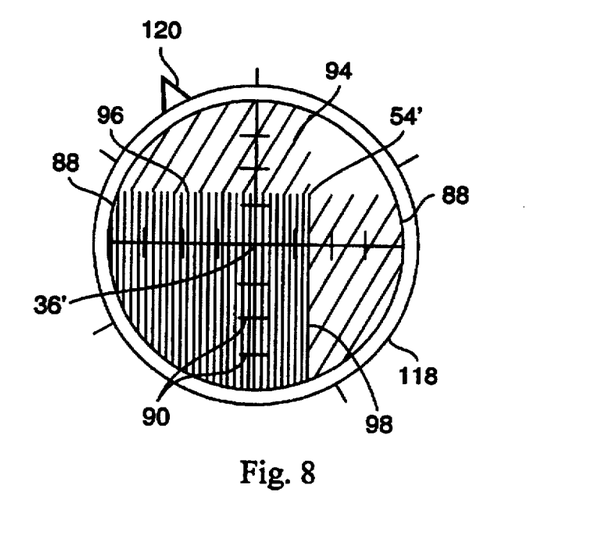
FIG. 8 shows a schematic view of the graphic object in a situation where a probe tip is below and to the left of a desired trajectory.

At task 114, indicators 88 and 94 represent logical constructions which may be carried out in memory 18 (see FIG. 1) and not actual visual images viewable through display 24 (see FIG. 1). Actual visual images are displayed later in accordance with a task 128, discussed below. Nevertheless, FIG. 8 shows a schematic view of graphic object 46 in a hypothetical situation where probe tip 36 is below and to the left of trajectory 54. The hypothetical situation depicted in FIG. 8 is consistent with the hypothetical situation depicted in FIG. 7. Unlike FIG. 2, FIG. 8 illustrates a situation where probe tip indicator 88 is not aligned with trajectory indicator 94. Probe tip point 36' of probe tip indicator 88 resides at a location below and to the left of trajectory point 54'. The direction in which to move probe tip 36 to cause probe tip 36 to intersect trajectory 54 will be indicated in the visual image to be displayed during an upcoming task through a graphic illustration.

In addition, trajectory indicator 94 is positioned relative to probe tip indicator 88 so that trajectory point 54' resides distance 108 (see FIG. 7) away from probe tip point 36' as expressed in accordance with distance-indicating feature 90 of probe tip indicator 88. Accordingly, the distance from probe tip 36 to trajectory 54 will be graphically indicated.

Figure 9:
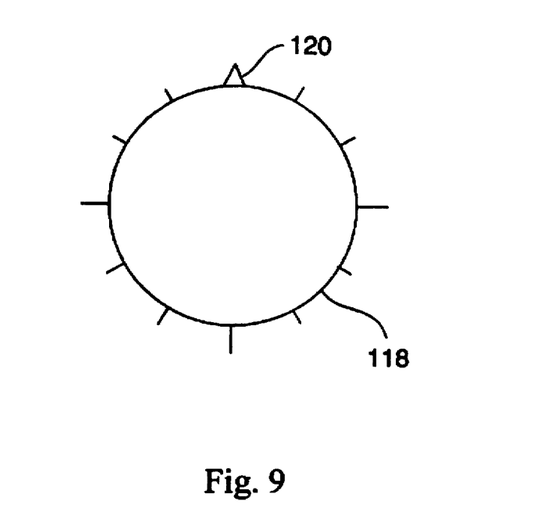
FIG. 9 shows a schematic view of a roll feature of the graphic object.

After task 114, a task 116 formulates and overlays a roll feature 118 on the graphic object formulated above in task 114 or in any other location which may be desirable. FIG. 9 illustrates roll feature 118 apart from other portions of graphic object 46. Roll feature 118 includes a pointer 120 which characterizes roll away from the initial roll angle obtained in task 76 (see FIG. 3). FIG. 9 depicts an orientation for roll feature 118 which represents no roll from the initial orientation. On the other hand, in FIG. 8 pointer 120 indicates a counterclockwise roll of approximately 30° from the original orientation.

Referring to FIG. 2, roll feature 118 coordinates graphic object 46 with live video image 44. The roll orientation indicated by roll feature 118 informs a surgeon which direction is up in live video image 44. When probe 12 is a round, straight instrument, roll feature 118 may not be needed for any purpose other than helping a surgeon maintain proper orientation while viewing live video images 44. Thus, roll feature 118 may alternatively be placed around live video image 44. However, in situations where probe 12 is not round or is not straight, roll orientation becomes more critical to the problem of guiding probe 12 to target 52. Consequently, for these situations roll feature 118 desirably operates as a portion of graphic object 46.

Referring to FIGS. 6–8, after task 116 a query task 122 evaluates distance 112 determined above in task 110 to determine whether probe tip 36 is near target 52. In the preferred embodiment, task 122 determines whether distance 112 is less than a predetermined value. This predetermined value corresponds to the maximum distance indicated by distance-indicating feature 90.

When task 122 determines that probe tip 36 is near target 52, a task 124 formulates and overlays a distance-to-target feature 126 on graphic object 46. FIG. 2 depicts feature 126 as a circle centered on probe tip point 36'. The radius of this circle is dimensioned in accordance with the scale defined through distance-indicating feature 90 to indicate distance 112.

As probe tip 36 initially approaches target 52, feature 126 may not be visible because probe tip 36 is not near target 52. This situation is depicted by an absence of feature 126 in FIG. 8. As probe tip 36 nears target 52, feature 126 becomes visible, and as probe tip 36 approaches target 52, distance-to-target feature 126 shrinks upon probe tip point 36'.

After task 124 and when task 122 determines that probe tip 36 is not yet near target 52, a task 128 causes graphic guidance object 46 to be displayed at display 24 (see FIG. 1). In other words, task 128 actually causes visual images similar to those depicted in FIGS. 2 and 8 to be produced. As discussed above, object 46 may include various indicators and features which provide a surgeon with useful guidance information. Object 46 visually illustrates a direction to move probe tip 36 to cause probe tip 36 to intersect trajectory 54. In addition, the distance to trajectory 54 is visually illustrated. Likewise, the distance to target 52 is visually illustrated, but only when probe tip 36 nears target 52. Moreover roll orientation is visually illustrated. In accordance with tasks 68 and 72 (see FIG. 3), object 46 may be displayed simultaneously with live video image 44 and tomogram image 42 (see FIG. 2).

Task 128 may additionally present other information at screen 40 (see FIG. 2). For example, current alphanumeric data 50 (see FIG. 2) may update a "position of probe tip" data field and a "distance to target" data field in screen 40.

After task 128, a query task 130 determines whether to refresh tomogram image 42 (see FIG. 2). If tomogram slices 42 are being displayed and system 10 determines that a new slice now needs to be displayed, then a task 132 displays the next tomogram slice. In addition, task 132 may perform other image processing tasks related to the tomogram image.

Procedure 100 performs a query task 134 after task 132 and when task 130 decides that tomogram image 42 does not need to be refreshed. Task 134 determines whether to exit track procedure 100. User input received through the operation of selection buttons 48 (see FIG. 2) may cause task 134 to exit track procedure 100. Such user input may be received at any time during the process of guiding probe 12 to target 52 as needed to revise the location of initial point 82, to re-align localizer 26, to alter the configuration of screen 40 such as by displaying different types of tomograms, to adjust parameters for the endoscope, and the like. In general, a surgeon may exit track process 100 at any time and repeat one or more of the tasks discussed above in connection with setup procedure 56 (see FIG. 3). In addition, such user input may be received when probe 12 has been guided to target 52.

When probe 12 has been guided to target 52, a surgeon may, for example, cause system 10 to exit procedure 100 and display a full screen view of live video image 44.

When task 134 determines that no user input has been received requesting an exit from procedure 100, program control loops back to task 102 to repeat procedure 100. As a result of continuously repeating procedure 100, procedure 100 causes system 10 to track movement of probe tip 36 in real time. Those skilled in the art will appreciate that the tasks discussed above in connection with procedure 100 require only relatively simple 2-D graphic techniques. Consequently, such calculations may be performed quickly by conventional personal computers so that no perceivable lag results between probe movement and the resulting depiction of a graphic guidance object in screen 40 (see FIG. 2).

In summary, the present invention provides an improved method and apparatus for guiding an instrument to a target. The present invention displays information to a user which indicates whether or not a surgical instrument is positioned along a specific trajectory. In addition, information that indicates in which direction to move a probe tip to cause a probe tip to intersect the specific trajectory is displayed. Trajectory guidance information is automatically presented in real time in response to probe movement. After setup, a surgeon may concentrate on the surgical instrument and the graphic guidance object and need not otherwise control the system. Live video endoscopic images and/or tomogram images may be simultaneously presented with the graphic guidance object.

The present invention has been described above with reference to preferred embodiments. However, those skilled in the art will recognize that changes and modifications may be made in these preferred embodiments without departing from the scope of the present invention. For example, those skilled in the art will appreciate that computer programs may be arranged in a wide variety of ways that do not necessarily resemble the precise program flow depicted herein but which nevertheless perform substantially equivalent functions. Moreover, those skilled in the art will appreciate that displayed information need not be configured precisely as described herein but that substantially equivalent information may be expressed and displayed in any number of different ways. These and other changes and modifications which are obvious to those skilled in the art are intended to be included within the scope of the present invention.

What is claimed is:

1. A method for presenting guidance information to a user engaged in guiding a probe to a target within a body, said method comprising the steps of:

identifying a location for said target;

identifying a location for an initial point;

determining a current location for a tip of said probe;

displaying a trajectory indicator, said trajectory indicator depicting a plane substantially perpendicular to a desired trajectory so that said desired trajectory appears as a single point in said plane, wherein said desired trajectory includes said target and said initial point locations; and displaying a probe tip indicator overlying said trajectory indicator, wherein said probe tip indicator corresponds to said tip of said probe and said trajectory indicator and said probe tip indicator feature together indicate a direction in which to move said probe tip to cause said probe tip to intersect said desired trajectory.

2. A method as claimed in claim 1 additionally comprising the step of:

positioning said trajectory indicator and said probe tip indicator relative to each other so that when said probe tip indicator is aligned with said trajectory indicator said probe tip besides on said desired trajectory.

3. A method as claimed in claim 1 additionally comprising the step of displaying a feature which indicates distance from said probe tip to said target.

4. A method as claimed in claim 1 additionally comprising the step of presenting at least one tomographic image while said displaying step displays said graphic object.

5. A method as claimed in claim 1 additionally comprising the step of repeating said determining step, said trajectory indicator displaying step, and said probe tip indicator displaying step to track movement of said probe tip in real time.

6. A method as claimed in claim 1 additionally comprising the step of defining said predetermined trajectory to be a substantially straight line.

7. A method as claimed in claim 1 wherein said trajectory indicator displaying step comprises the step of configuring said plane into four quadrants so that said single point appearance of said desired trajectory is common to said four quadrants.

8. A method for presenting guidance information to a user engaged in guiding a probe to a target within a body, said method comprising the steps of:

identifying coordinates of said target;

identifying coordinates of an entry point into said body;

determining current coordinates for a tip of said probe;

controlling a display to form a graphic object therein that indicates a direction in which to move said probe tip to cause said probe tip to intersect a predetermined trajectory which includes said target and said entry point coordinates and to form a feature in said graphic object which indicates distance from said probe tip to said target; and repeating said determining and controlling steps to track movement of said probe tip.

9. A method for presenting guidance information to a user engaged in guiding a probe to a target within a body, said probe being configured to generate live video images, and said method comprising the steps of:

identifying coordinates of said target;

identifying coordinates of an entry point into said body;

determining current coordinates for a tip of said probe;

controlling a display to indicate a direction in which to move said probe tip to cause said probe tip to intersect a predetermined trajectory which includes said target and said entry point coordinates;

repeating said determining and controlling steps to track movement of said probe tip; and presenting said live video images in said display while said controlling step causes said display to indicate said direction in which to move said probe tip to cause said probe tip to intersect said predetermined trajectory.

10. An apparatus for presenting guidance information to a user engaged in guiding a probe to a target within a body, said apparatus comprising:

means for identifying a location for said target;

a localizer configured at least in part to identify a location for an initial point relative to said body;

a controller, coupled to said localizer and to said identifying means, said controller being configured to determining a current location for a tip of said probe and to determine a direction in which to move said probe tip to cause said probe tip to intersect a desired trajectory which includes said target and said initial point locations; and a display, coupled to said controller, for displaying a trajectory indicator, said trajectory indicator depicting a plane substantially perpendicular to said desired trajectory so that said desired trajectory appears as a single point in said plane, and for displaying a probe tip indicator overlying said trajectory indicator, wherein said probe tip indicator corresponds to said probe tip and said trajectory indicator and said probe tip indicator feature together indicate a graphic object which illustrates said direction in which to move said probe tip to cause said probe tip to intersect said desired trajectory.

11. An apparatus as claimed in claim 10 wherein said controller is further configured to form said graphic object to include a feature which indicates distance from said probe tip to said target.

12. An apparatus for presenting guidance information to a user engaged in guiding a probe configured to generate live video images to a target within a body, said apparatus comprising:

means for identifying a location for said target;

a localizer configured at least in part to identify a location for an initial point relative to said body;

a controller means, coupled to said localizer, said probe, and said identifying means, for determining a current location for a tip of said probe and for determining a direction in which to move said probe tip to cause said probe tip to intersect a predetermined trajectory which includes said target and said initial point locations, and said controller means further causing said display to present said live video images while simultaneously displaying a graphic object which illustrates said direction in which to move said probe tip to cause said probe tip to intersect said predetermined trajectory; and a display, coupled to said controller, for displaying said graphic object.

13. A method for presenting guidance information to a user engaged in guiding a probe to a target within a body, said method comprising the steps of:

identifying a location for said target;

identifying a location for an initial point;

determining a current location for a tip of said probe;

displaying a graphic object which indicates a direction in which to move said probe tip to cause said probe tip to intersect a predetermined trajectory which includes said target and said initial point locations; and forming a feature in said graphic object which indicates distance from said probe tip to said predetermined trajectory.

14. A method for presenting guidance information to a user engaged in guiding a probe to a target within a body, said method comprising the steps of:

identifying a location for said target;

identifying a location for an initial point;

identifying an initial roll orientation for said probe;

determining a current location for a tip of said probe and a current roll orientation for said probe;

displaying a graphic object which indicates a direction in which to move said probe tip to cause said probe tip to intersect a desired trajectory which includes said target and said initial point locations; and forming a display feature which is responsive to said current roll orientation of said probe relative to said initial roll orientation.

15. A method for presenting guidance information to a user engaged in guiding a probe to a target within a body, said probe being configured to generate live video images, and said method comprising the steps of:

identifying a location for said target;

identifying a location for an initial point;

determining a current location for a tip of said probe;

displaying a graphic object which indicates a direction in which to move said probe tip to cause said probe tip to intersect a predetermined trajectory which includes said target and said initial point locations; and presenting said live video images while said displaying step displays said graphic object.

\* \* \* \* \*

UNITED STATES PATENT AND TRADEMARK OFFICE
CERTIFICATE OF CORRECTION

PATENT NO.  : 5,638,819
DATED       : June 17, 1997
INVENTOR(S) : Kim H. Manwaring and Mark L. Manwaring It is certified that error appears in the above-indentified patent and that said Letters Patent is hereby corrected as shown below:

In the Column 12, Line 4:

please delete "besides" and insert --resides--

Signed and Sealed this

Second Day of September, 1997

Attest:

BRUCE LEHMAN

Attesting Officer    Commissioner of Patents and Trademarks